(12) United States Patent
Wu et al.

(10) Patent No.: US 11,504,235 B2
(45) Date of Patent: Nov. 22, 2022

(54) AUXILIARY BALLOON STRUCTURE FOR TRANSCATHETER AORTIC VALVE REPLACEMENT (TAVR)

(71) Applicant: FUWAI HOSPITAL CHINESE ACADEMY OF MEDICAL SCIENCES, Beijing (CN)

(72) Inventors: Yongjian Wu, Beijing (CN); Qingrong Liu, Beijing (CN)

( * ) Notice: Subject to any disclaimer, the term of this patent is extended or adjusted under 35 U.S.C. 154(b) by 120 days.

(21) Appl. No.: 16/885,285

(22) Filed: May 28, 2020

(65) Prior Publication Data
US 2021/0330458 A1 Oct. 28, 2021

(30) Foreign Application Priority Data

Apr. 27, 2020 (CN) .......................... 202010346508.2

(51) Int. Cl.
*A61F 2/24* (2006.01)
*A61M 25/10* (2013.01)

(52) U.S. Cl.
CPC ............ *A61F 2/2433* (2013.01); *A61M 25/10* (2013.01); *A61F 2230/0065* (2013.01); *A61F 2230/0067* (2013.01); *A61F 2230/0069* (2013.01); *A61F 2250/0029* (2013.01); *A61M 25/1002* (2013.01); *A61M 25/104* (2013.01); *A61M 2025/1086* (2013.01)

(58) Field of Classification Search
CPC .............. A61M 25/10; A61M 25/1002; A61M 25/104; A61M 2025/1086; A61F 2/2433; A61F 2230/0065; A61F 2230/0067; A61F 2230/0069; A61F 2250/0029
See application file for complete search history.

(56) References Cited

U.S. PATENT DOCUMENTS 9,925,328 B2 * 3/2018 Jang ...................... A61M 5/007
2020/0215310 A1 * 7/2020 Rentschler ........ A61M 25/1002

* cited by examiner

*Primary Examiner* — Suzette J Gherbi

(57) ABSTRACT

The invention discloses an auxiliary balloon structure for transcatheter aortic valve replacement (TAVR), which comprises a balloon head and a balloon body. When unexpanded, the balloon body has two conical ends and a cylindrical middle part. The conical ends are defined as a front and a rear conical part. The cylindrical middle part is provided with a mastoid structure. The front and rear conical parts are made of a semi-compliant material, while the cylindrical middle part is made of a non-compliant material.

13 Claims, 6 Drawing Sheets

AUXILIARY BALLOON STRUCTURE FOR TRANSCATHETER AORTIC VALVE REPLACEMENT (TAVR)

RELATED APPLICATION

The application claims the benefit of the Chinese Patent Application CN202010346508.2 filed Apr. 27, 2020, which is incorporated herein by reference in its entirety.

FIELD OF THE INVENTION

The present invention relates to the technical field of medical instruments, in particular to an auxiliary balloon structure for transcatheter aortic valve replacement (TAVR).

BACKGROUND OF THE INVENTION

Transcatheter aortic valve replacement (TAVR) adopts a minimally invasive cardiac interventional catheter technique to perform artificial interventional heart valve replacement, has advantages such as no chest opening, low risk, simple operation, small trauma, fast recovery and few complications, and is especially suitable for patients with surgical contraindications or high-risk surgical patients.

In TAVR surgery, due to exceptional anatomical features of a valve and an aortic root, the local anatomical tissues of some patients are relatively hard, so that the balloon may slip during pre-expanding and therefore expand undesirably or fail to effectively expand. Such a condition will exert a strong impact on the release of a TAVR valve stent in the TAVR surgery, especially for a self-expanding artificial intervention heart valve. This may cause a failure in effective fit between the valve stent and the aorta wall after TAVR, that is, perivalvular leakage, to thereby affect the function of the heart valve. From a long-term perspective, the failure in effective expanding of the valve stent will lead to self-expanding of the valve stent in an irregular shape, and thus affect the shape and operation of the artificial valve, which is likely to increase fatigue of the artificial valve and consequently shortens the life of the artificial heart valve.

OBJECTS AND SUMMARY OF THE INVENTION

In view of the defects in prior arts, the present invention provides an auxiliary balloon structure for transcatheter aortic valve replacement (TAVR), which can avoid slip during expansion of the balloon to ensure a good expanding effect. The balloon structure has accurate locating functions, especially suitable for calcification lesions, and can improve the success rate of the TAVR surgery.

An auxiliary balloon structure for TAVR comprises a balloon head and a balloon body. When unexpanded, the balloon body has two conical ends and a cylindrical middle part. The conical ends are defined as a front and a rear conical part. The cylindrical middle part is provided with a mastoid structure. The front and rear conical parts are made of a semi-compliant material, while the cylindrical middle part is made of a non-compliant material.

The auxiliary balloon structure further comprises a catheter. The balloon body is in sealed connection with one end of the catheter by thermal welding or laser welding. On the catheter, the balloon head is located on the outer side of the balloon body and sealed with the head of one end of the catheter.

In the auxiliary balloon structure, the front and rear conical parts are made of a polyamide polymer material, and the cylindrical middle part is made of an improved polyamide polymer composite material.

In the auxiliary balloon structure, the cylindrical middle part is classified on the basis of external diameter into five models, i.e. 16 mm, 18 mm, 20 mm, 22 mm, 24 mm and 26 mm, and has a length of 40 mm.

In the auxiliary balloon structure, the mastoid structure comprises multiple mastoid rings, the same one mastoid ring comprises three mastoid groups, and the three mastoid groups are distributed at 120 degrees relative to each other circumferentially on the section of the cylindrical middle part in the position of a given mastoid ring.

In the auxiliary balloon structure, each mastoid group includes 6-10 mastoids arranged in a single row, and all the mastoids of each mastoid ring are located on the same section of the cylindrical middle part.

In the auxiliary balloon structure, the interval between the adjacent two mastoids of each mastoid group is 2 mm.

In the auxiliary balloon structure, the heights of the mastoids are 1.0 mm-1.5 mm.

In the auxiliary balloon structure, a mastoid array is arranged in the area between the adjacent two mastoid rings, and comprises multiple array units; and each array unit comprises at least four mastoids including a central mastoid and at least three surrounding mastoids distributed around the central mastoid.

In the auxiliary balloon structure, the height of the central mastoid is 1.5 mm and the heights of the surrounding mastoids are 1.0 mm.

In the auxiliary balloon structure, a hydrophilic coating layer is applied outside the catheter.

In the auxiliary balloon structure, the other end of the catheter is provided with two connectors, i.e. first connector and second connector; and the first connector is used for connecting with a gas phase pressure source or liquid phase pressure source, and the second connector is used for insertion of a guide wire.

In the auxiliary balloon structure, the second connector is arranged coaxial with the catheter.

In the auxiliary balloon structure, the balloon body is provided with a mark; and the catheter is provided with a gas outlet in the balloon body.

The auxiliary balloon structure for TAVR can assist an operator to well effectively pre-expand the balloon before TAVR surgery and has a high clinical practical significance.

Reference signs: 1. Balloon head; 2. Balloon body; 3. Front conical part; 4. Rear conical part; 5. Cylindrical middle part; 6. Mastoid structure; 7. Catheter; 8. Mastoid group; 9. Central mastoid; 10. Surrounding mastoid; 11. First connector; 12. Second connector; 13. Guide wire; 14. Mark; 15. Array unit

DETAILED DESCRIPTION OF THE EMBODIMENTS

Hereinafter, embodiments of the present invention will be described in details in conjunction with the accompanying drawings.

In prior arts, when the balloon expands, it may slip or fail to effectively expand, resulting in a failure in desired pre-expansion. In order to at least solve the technical problems of slip or failure in effective expansion, a detailed description will be given in the following embodiments.

Figure 1:
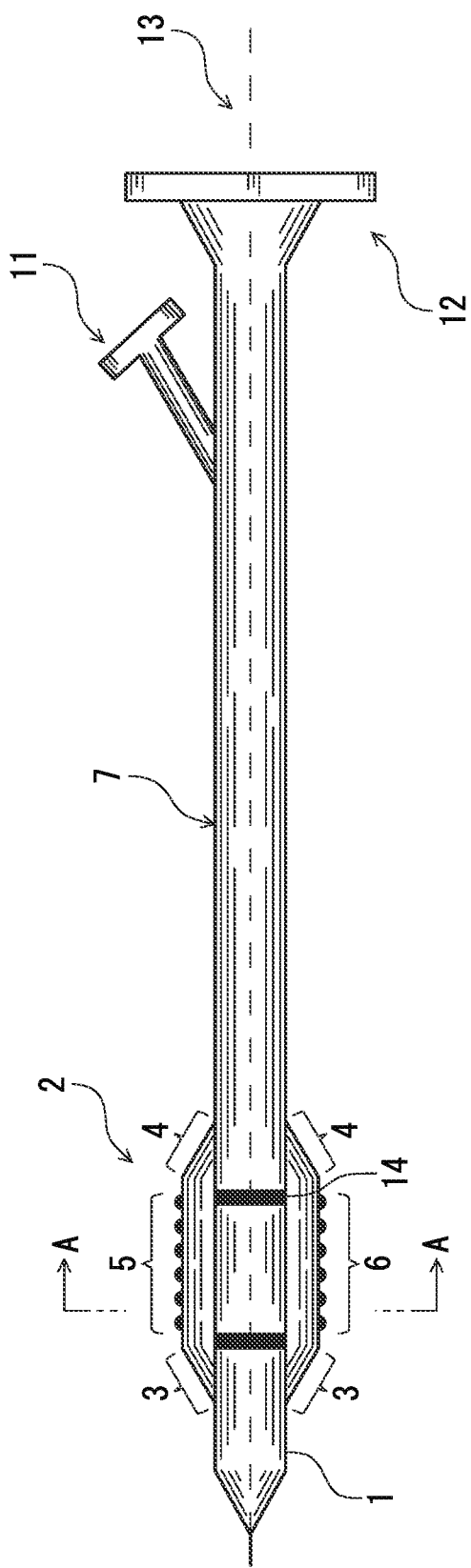
FIG. 1 is a schematic diagram of the auxiliary balloon structure provided in one embodiment of the present invention.

An auxiliary balloon structure for transcatheter 7 aortic valve replacement (TAVR) is provided in the embodiment, as shown in FIG. 1. The balloon structure comprises a balloon head 1 and a balloon body 2. When unexpanded, the balloon body 2 has two conical ends and a cylindrical middle part 5. The conical ends are defined as a front conical part 3 and a rear conical part 4; the cylindrical middle part 5 is provided with a mastoid structure 6; and the front conical part 3 and the rear conical part 4 are made of a semi-compliant material, while the cylindrical middle part 5 is made of a non-compliant material.

The balloon head 1 has an external diameter smaller than that of the balloon body 2; the front conical part 3 and the rear conical part 4 are made of a semi-compliant material, while the cylindrical middle part 5 is made of a non-compliant material, so that different parts have different compliance; during inflation, the front conical part 3 and the rear conical part 4 expand first to play the role in temporary fixing and prevent the balloon from slipping; and the cylindrical middle part 5 expands to a small extent under a relatively high pressure during further inflation, and the contact between the balloon structure and the aorta is increased in the presence of the mastoid structure 6, to play the role in fixing, thereby achieving accurate positioning and slip prevention.

With reference to FIG. 1 again, the balloon structure further comprises a catheter 7. The balloon body 2 is in sealed connection with one end of the catheter 7 by thermal welding or laser welding; on the catheter 7, the balloon head 1 is located on the outer side of the balloon body 2 and sealed with the head of one end of the catheter 7; the balloon body 2 is provided with a mark 14; and the catheter 7 is provided with a gas outlet in the balloon body 2.

With further reference to FIG. 1, in some embodiments, a hydrophilic coating layer is applied outside the catheter 7 to facilitate delivery of the catheter 7 and reduce damage to the blood vessel, while no hydrophilic coating is required on the outer layer of the balloon structure. The other end of the catheter 7 is provided with two connectors, i.e. first connector 11 and second connector 12; the first connector 11 is used for connecting with a gas phase pressure source or liquid phase pressure source; the catheter 7 is provided therein with a guide wire 13 passage, the second connector 12 is used for insertion of the guide wire 13, the guide wire 13 is located in the guide wire 13 passage, and the balloon structure can be delivered to a proper part along the track of the guide wire 13 during surgery; and the second connector 12 is arranged coaxial with the catheter 7.

In some embodiments, the catheter 7 can serve as a delivery rod in surgery and is made of a metal material such as stainless steel and nickel titanium alloy.

In some embodiments, the front conical part 3 and the rear conical part 4 are made of a polyamide polymer material; and the cylindrical middle part 5 is made of an improved polyamide polymer composite material.

In some embodiments, through clinical experience and summary of practical applications, the cylindrical middle part 5 is preferably classified on the basis of external diameter into five models, i.e. 16 mm, 18 mm, 20 mm, 22 mm, 24 mm and 26 mm, in order to adapt to different patients or different internal diameters of blood vessels; and the length of the cylindrical middle part 5 is 40 mm.

Figure 2:
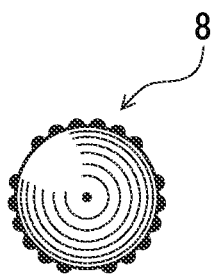
FIG. 2 is an A-A sectional view of FIG. 1.

In some embodiments, the mastoid structure 6 comprises multiple mastoid rings, the same one mastoid ring comprises three mastoid groups 8, and as shown in FIG. 2, the three mastoid groups 8 are distributed at 120 degrees relative to each other circumferentially on the section of the cylindrical middle part 5 in the position of a given mastoid ring.

With further reference to FIG. 2, in some embodiments, each mastoid group 8 comprises 6 mastoids arranged in a single row, and all the mastoids of each mastoid ring are located on the same section of the cylindrical middle part 5.

In some preferred embodiments, the interval between the adjacent two mastoids of each mastoid group 8 is 2 mm.

In an optional embodiment mentioned above, the heights of the mastoids are 1.0 mm-1.5 mm.

Figure 3:
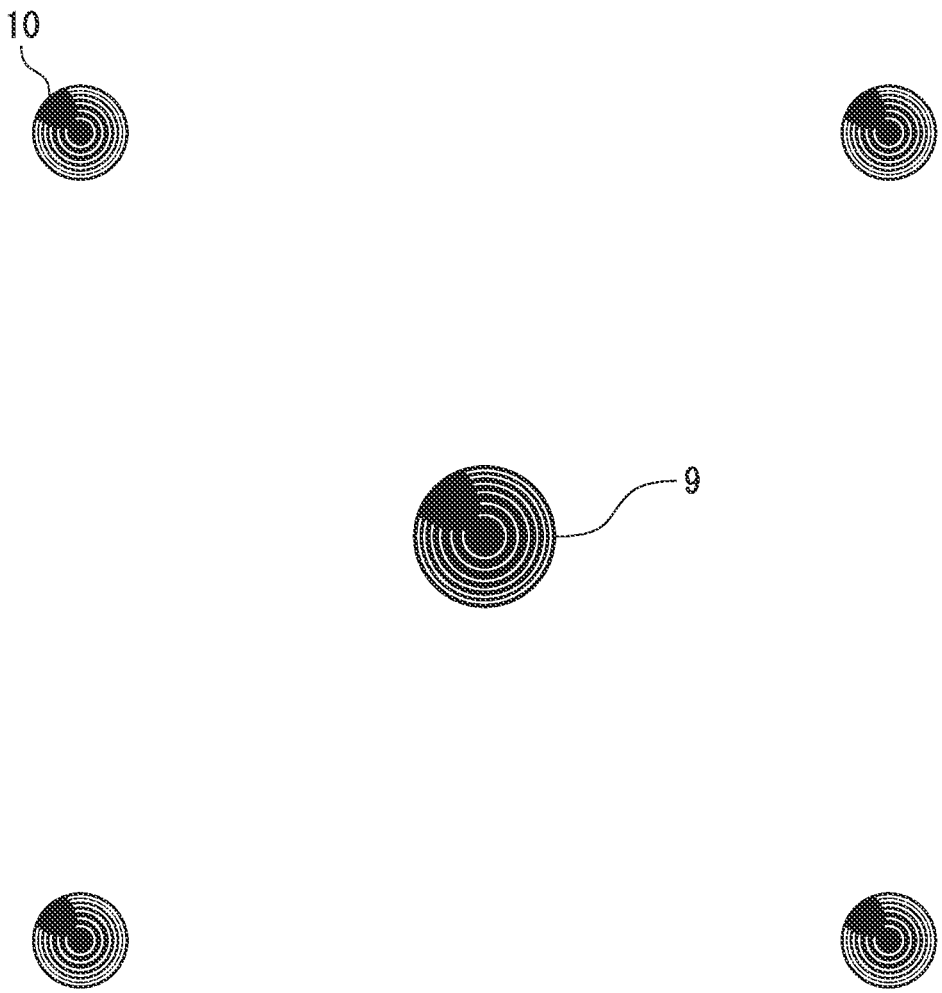
FIG. 3 is a schematic diagram of the array unit provided in one embodiment of the present invention.

As a preferred embodiment of the above embodiments, a mastoid array is arranged in the area between the adjacent two mastoid rings, and comprises multiple array units 15; as shown in FIG. 3, each array unit 15 comprises five mastoids including a central mastoid 9 and four surrounding mastoids 10 distributed around the central mastoid 9; the central mastoid 9 is higher than the surrounding mastoids 10; preferably, the height of the central mastoid 9 is 1.5 mm; and the heights of the surrounding mastoids 10 are 1.0 mm.

Figure 4:
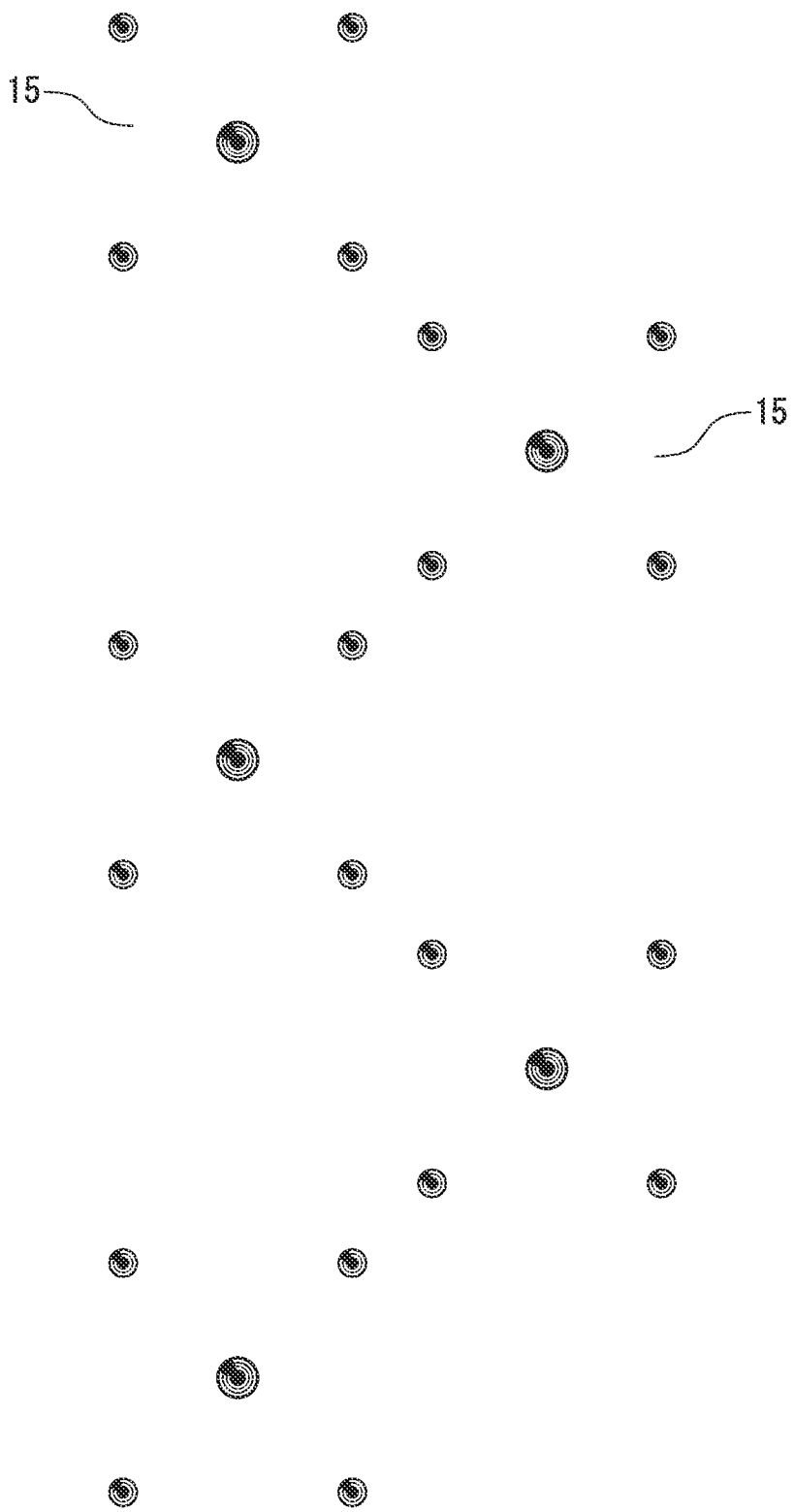
FIG. 4 is a schematic diagram of array distribution of the multiple array units in the area between the adjacent two mastoid rings in one embodiment of the present invention.

As shown in FIG. 4, the adjacent two rows of the multiple array units 15 are staggered, that is, the $a^{th}$ array unit 15 in an $(N\pm1)^{th}$ row is arranged between the $a^{th}$ array unit 15 and the $(a+1)^{th}$ array unit 15 in an $N^{th}$ row, but at a one-row distance to the left or right.

In all the above embodiments, the mastoid structure 6 is arranged for slip prevention and accurate positioning.

The inventive balloon structure for transcatheter 7 aortic valve replacement (TAVR) can accurately locate, prevent slip and especially suitable for calcification lesions, improve the success rate of TAVR, and reduce the incidence of complications such as artificial intervention heart valve replacement or post-operative perivalvular leakage. The release of an artificial intervention heart valve stent in a good form enables the artificial valve to work well, and can prolong the service life of the artificial heart valve at the same time.

Figure 5:
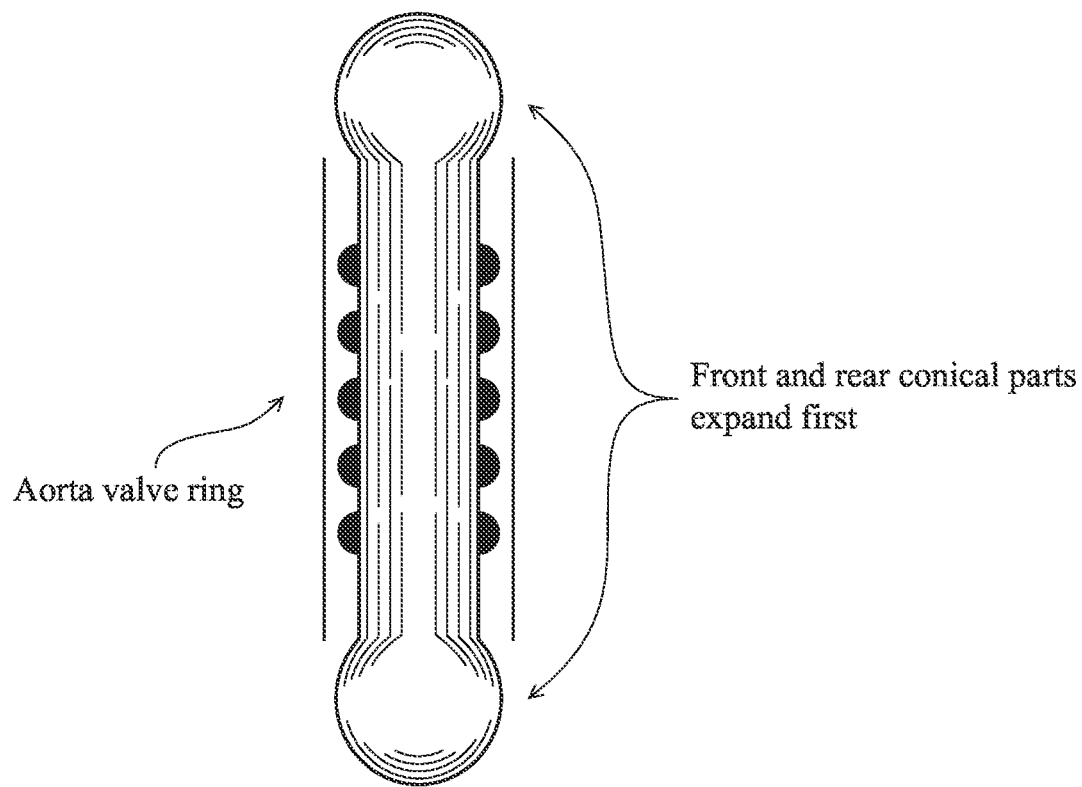
FIG. 5 is a schematic diagram of the auxiliary balloon structure in a temporary fixation state at an early pressurization stage in one embodiment of the present invention.
Figure 6:
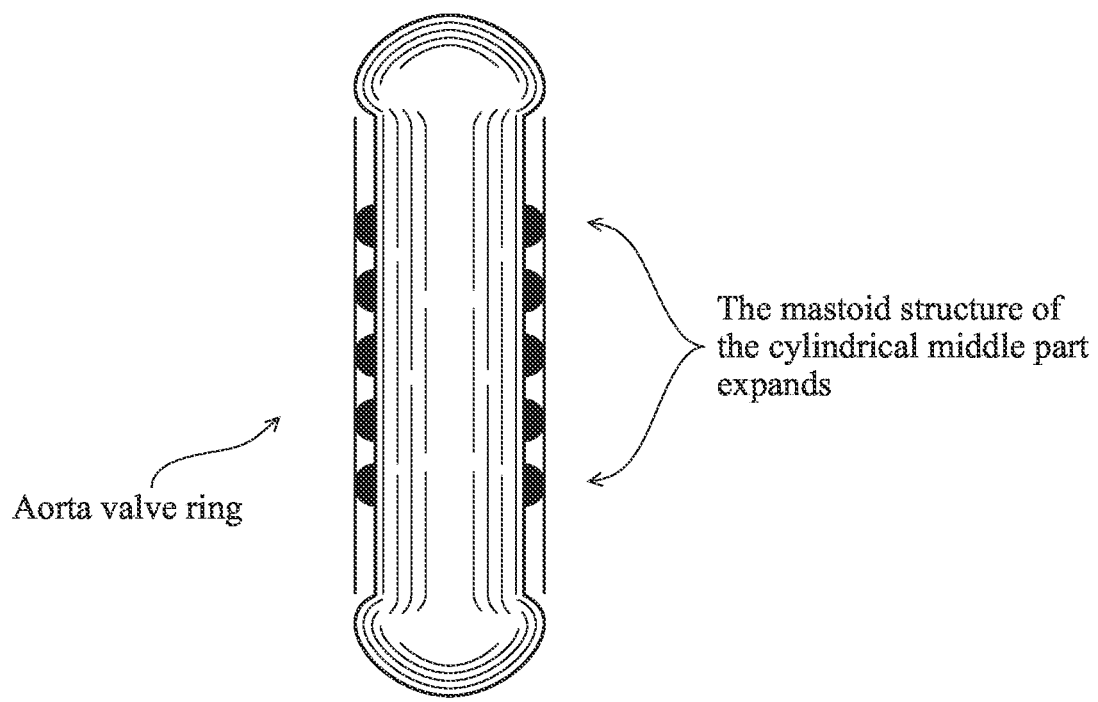
FIG. 6 is a schematic diagram of the auxiliary balloon structure in a balloon positioning and expanding state at a late pressurization stage in one embodiment of the present invention.

As shown in FIGS. 5 and 6, when the balloon structure is inflated via the first connector 11 of the catheter 7, the front conical part 3 and the rear conical part 4 both made of a semi-compliant material expand first to play the role in temporary fixing and prevent the balloon from slipping; and the cylindrical middle part 5 made of a non-compliant material expands to a small extent under a relatively high pressure during further inflation, and the contact between the balloon structure and the aorta is increased in the presence of the mastoid structure 6 in contact with the aorta valve ring, to play the role in fixing, thereby achieving accurate positioning and slip prevention.

The embodiments mentioned above are only used to illustrate the technical solution of the present invention, but not limited thereto. Although the present invention has been described in detail with reference to the foregoing embodiments, those skilled in the art should understand that modifications can be made on the technical solutions described in the foregoing embodiments, or equivalent replacements can be made on some or all of the technical features. These modifications or replacements do not make the essence of the corresponding technical solutions deviate from the scope of the technical solutions of the embodiments of the present invention, and should be covered by the scope of the claims and the specification of the present invention.

What is claimed is:

1. An auxiliary balloon structure located at one end of a catheter, for use in transcatheter aortic valve replacement (TAVR), comprising a balloon head and a balloon body, wherein:
   when unexpanded, the balloon body has two conical ends and a cylindrical middle part;
   the conical ends are defined by a front conical part and a rear conical part; the front and rear conical parts are made of a semi-compliant material;
   the cylindrical middle part is made of a non-compliant material and is provided with a mastoid structure which comprises multiple mastoid rings, each mastoid ring comprises three mastoid groups, the three mastoid groups are distributed at 120 degrees relative to each other circumferentially on a section of the cylindrical middle part in a position of the given mastoid ring; a mastoid array is arranged in an area between adjacent two mastoid rings, the mastoid array comprises multiple array units, each array unit comprises multiple mastoids which include a central tall mastoid and shorter surrounding mastoids located around the central mastoid;
   each mastoid group includes 6-10 mastoids arranged in a single row, all the mastoids of each mastoid ring are located on the same section of the cylindrical middle part, the interval between the adjacent two mastoids of each mastoid group is 2 mm and the height of the mastoids is 1.0 mm or 1.5 mm; and
   the conical ends of the balloon body expand first and the cylindrical middle part expands later and when inflated the mastoid structure acts as anchoring part of the balloon structure to secure the balloon structure at a suitable position in aorta wall.

2. The balloon structure in claim 1, wherein:
   the balloon body is in sealed connection with the one end of the catheter by thermal welding or laser welding; and
   on the catheter, the balloon head is located outside of the balloon body and the balloon body is sealed with the balloon head at the one end of the catheter.

3. The balloon structure in claim 2, wherein:
   the front and rear conical parts are made of a polyamide polymer material; and
   the cylindrical middle part is made of a polyamide polymer composite material.

4. The balloon structure in claim 3, wherein the cylindrical middle part has a length of 40 mm.

5. The balloon structure in claim 2, wherein: each array unit comprises at least four mastoids including the central mastoid and at least three surrounding mastoids distributed around the central mastoid.

6. The balloon structure in claim 5, wherein:
   the height of the central mastoid is 1.5 mm: and
   the height of the surrounding mastoids is 1.0 mm.

7. The balloon structure in claim 6, wherein a hydrophilic coating layer is applied outside the catheter.

8. The balloon structure in claim 7, wherein:
   other end of the catheter is provided with a first connector and a second connector;
   the first connector is used for connecting with a gas phase pressure source or liquid phase pressure source; and
   the second connector is used for insertion of a guide wire.

9. The balloon structure in claim 8, wherein the cylindrical middle part has an external diameter of 16 mm.

10. The balloon structure in claim 9, wherein the cylindrical middle part has an external diameter of 18 mm.

11. The balloon structure in claim 10, wherein the cylindrical middle part has an external diameter of 20 mm.

12. The balloon structure in claim 11, wherein the cylindrical middle part has an external diameter of 24 mm.

13. The balloon structure in claim 12, wherein the cylindrical middle part has an external diameter of 26 mm.

* * * * *